United States Patent
Muhammed et al.

(10) Patent No.: US 11,433,024 B2
(45) Date of Patent: Sep. 6, 2022

(54) LIQUID ORAL PHARMACEUTICAL DOSAGE FORM

(71) Applicant: Johnson & Johnson Consumer Inc., Skillman, NJ (US)

(72) Inventors: Salih Muhsin Muhammed, Hyllinge (SE); Katarina Lindell, Eslöv (SE); Jill Nilgard, Helsingborg (SE); Sofi Nöjd, Helsingborg (SE)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 17/050,470

(22) PCT Filed: Apr. 24, 2019

(86) PCT No.: PCT/IB2019/053386
§ 371 (c)(1),
(2) Date: Oct. 26, 2020

(87) PCT Pub. No.: WO2019/207506
PCT Pub. Date: Oct. 31, 2019

(65) Prior Publication Data
US 2021/0106524 A1    Apr. 15, 2021

(30) Foreign Application Priority Data
Apr. 27, 2018   (SE) .................... 1850511-5

(51) Int. Cl.

| | |
|---|---|
| *A61K 9/10* | (2006.01) |
| *A61K 31/341* | (2006.01) |
| *A61K 31/4164* | (2006.01) |
| *A61K 31/426* | (2006.01) |
| *A61K 33/08* | (2006.01) |
| *A61K 33/10* | (2006.01) |
| *A61K 47/10* | (2017.01) |
| *A61K 47/14* | (2017.01) |
| *A61K 47/24* | (2006.01) |
| *A61K 47/38* | (2006.01) |
| *A61K 47/44* | (2017.01) |
| *A61K 47/46* | (2006.01) |
| *A61P 1/04* | (2006.01) |

(52) U.S. Cl.
CPC .............. *A61K 9/10* (2013.01); *A61K 31/341* (2013.01); *A61K 31/4164* (2013.01); *A61K 31/426* (2013.01); *A61K 33/08* (2013.01); *A61K 33/10* (2013.01); *A61K 47/10* (2013.01); *A61K 47/14* (2013.01); *A61K 47/24* (2013.01); *A61K 47/38* (2013.01); *A61K 47/44* (2013.01); *A61K 47/46* (2013.01); *A61P 1/04* (2018.01)

(58) Field of Classification Search
None
See application file for complete search history.

(56) References Cited

U.S. PATENT DOCUMENTS

| | | |
|---|---|---|
| 5,229,137 A | 7/1993 | Wolfe |
| 5,817,340 A | 10/1998 | Roche et al. |
| 5,976,578 A | 11/1999 | Beyerle et al. |
| 6,267,985 B1 | 7/2001 | Chen et al. |
| 6,589,551 B1 | 7/2003 | Jolliffe |
| 2013/0108694 A1* | 5/2013 | Chou ................... A61K 9/0053 424/452 |
| 2015/0224056 A1* | 8/2015 | Tidmarsh ............... A61K 9/209 514/370 |
| 2018/0140630 A1 | 5/2018 | Wolfe et al. |

FOREIGN PATENT DOCUMENTS

| | | |
|---|---|---|
| EP | 0664701 B | 8/1995 |
| EP | 0990438 A | 4/2000 |
| EP | 1992345 A | 11/2008 |
| EP | 2085079 A | 8/2009 |
| GB | 2218333 A | 11/1989 |
| WO | WO 92/04893 A | 4/1992 |
| WO | WO 93/21932 A | 11/1993 |
| WO | WO 96/02262 A | 2/1996 |
| WO | WO 2004/035090 A | 4/2004 |
| WO | WO 2008/134013 A | 11/2008 |
| WO | WO 2016/196205 A | 12/2016 |
| WO | WO 2018/083583 A | 5/2018 |

OTHER PUBLICATIONS

"Maalox Advanced Maximum Strength Mint" an internet article obtained from the website: https://www.drugs.com/otc/130131/maalox-advanced-maximum-strength-mint.html (Year: 2013).*
Swedish search report and written opinion for SE 1850511-5 dated Oct. 25, 2018.
International search report and written opinion for PCT/IB2019/053386 dated Apr. 24, 2019.
EP extended search report dated Dec. 17, 2021, for EP 19793833.5.

* cited by examiner

*Primary Examiner* — Sin J Lee

(57) ABSTRACT

A liquid oral pharmaceutical dosage form, comprising pharmacologically effective amounts of at least one histamine H2-receptor antagonist in a hydrophobic/lipophilic liquid substantially free from water comprising at least one viscosity enhancing agent, and pharmacologically effective amounts of one or more antacid(s) in a liquid comprising at least one viscosity enhancing agent and at least one flavor, wherein the two liquids are physically separated from each other and wherein the two liquids have matching rheological profiles and a package comprising multiple liquid oral dosage forms as well as a method of treating a gastric disease or disorder by use of the liquid oral pharmaceutical dosage form.

18 Claims, 1 Drawing Sheet

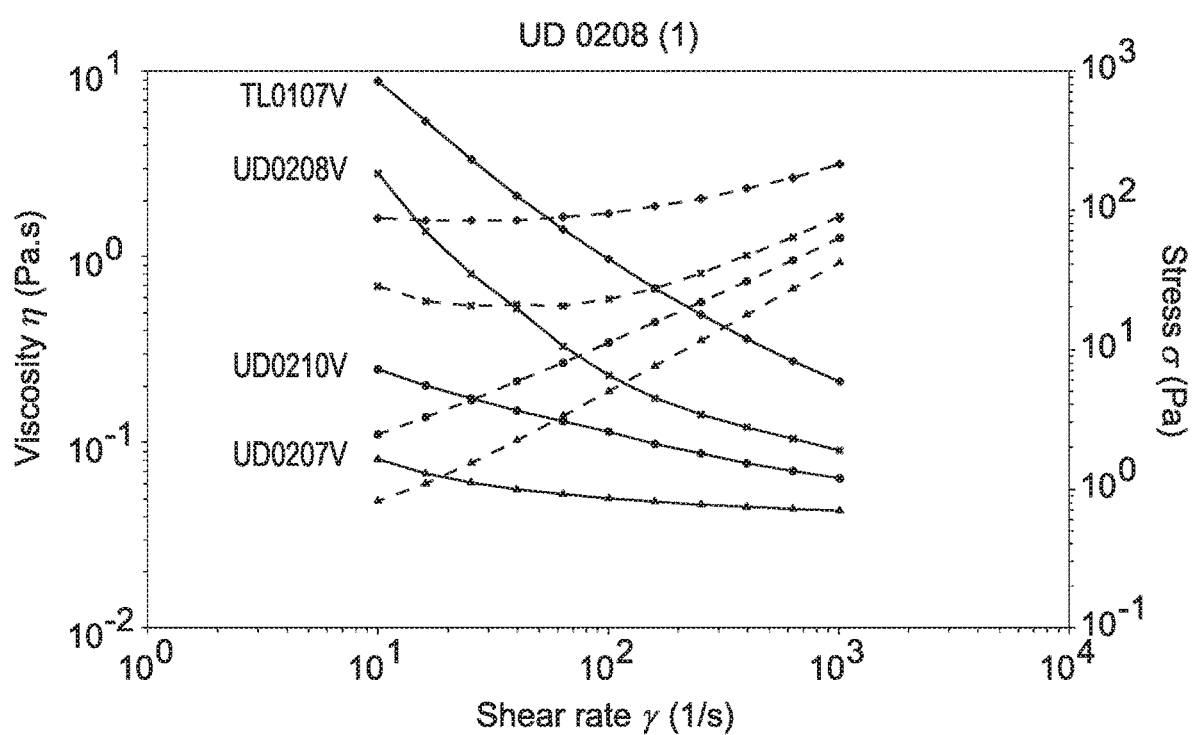

LIQUID ORAL PHARMACEUTICAL DOSAGE FORM

CROSS-REFERENCE TO RELATED APPLICATIONS

This application is the national stage filing under 35 USC 371 of international application PCT/IB2019/053386 filed on Apr. 24, 2019, which claims priority to SE 1850511-5 filed on Apr. 27, 2018, the complete disclosures of which are hereby incorporated by references for all purposes.

FIELD OF INVENTION

A liquid oral pharmaceutical dosage form, comprising pharmacologically effective amounts of at least one histamine H2-receptor antagonist in a hydrophobic/lipophilic liquid substantially free from water comprising at least one viscosity enhancing agent, and pharmacologically effective amounts of one or more antacid(s) in a liquid comprising at least one viscosity enhancing agent and at least one flavor, wherein the two liquids are physically separated from each other and wherein the two liquids have matching rheological profiles and a package comprising multiple liquid oral dosage forms as well as a method of treating a gastric disease or disorder by use of the liquid oral pharmaceutical dosage form.

BACKGROUND OF INVENTION

Histamine H2-receptor antagonists, for example cimetidine, ranitidine, nizetidine, roxatine and famotidine, reduce acid secretion by acting directly on the acid-secreting parietal cell located within the gastric gland of the stomach wall.

Although histamine H2-receptor antagonists are remarkably effective in the treatment of many gastric disorders, in particular peptic and gastric ulcers, there exist certain patient groups which do not respond to treatment. In addition, the time lapse between dosing and onset of action, limits the potential benefit of histamine H2-receptor antagonists in the treatment of acute, self-limiting gastric disorders.

Histamine H2-receptor antagonists are of potential benefit in the self-medication of acute, self-limiting gastric disorders such as hyperacidity. However, their slow onset of action is unlikely to meet the consumer requirement for rapid relief of symptoms.

Co-administration of histamine H2-receptor antagonists and other pharmaceutically active materials, including antacids, has been investigated. The rationale for co-administration with antacid is that the antacid brings about rapid relief from the symptoms of excess stomach acidity by neutralization whereas the histamine H2-receptor antagonist acts independently by inhibiting secretion of acid from the parietal cell.

Antacids used today are made from a variety of inorganic salts such as calcium carbonate, sodium bicarbonate, magnesium salts and aluminum salts. Magnesium hydroxide and aluminum hydroxide are the most potent magnesium and aluminum salts and are often used in combination. In addition, magnesium oxide, magnesium carbonate, aluminum phosphate, magaldrate, magnesium trisilicate, and aluminum sucrose sulfate (sucralfate) are also employed.

Until recently it has been impossible to co-administrate histamine H2-receptor antagonists, such as famotidine with antacids in a liquid form. It is well-known that histamine H2-receptor antagonist, i.e., famotidine is very unstable and thus difficult to produce a stable liquid formulation. Famotidine starts to degrade upon contact with water or any hydrolyzing agent as well as the antacids. So far there has been no product on the market comprising famotidine in a liquid form due to the stability problems. There have been reports on the stability problem, when famotidine is dissolved in a liquid. Antacids can be provided in the liquid form dissolved in a water-based liquid without any stability problem.

There have been many attempt to solve the above mentioned medical problem of heartburn and formulation problem, including stability, bitter taste without success including the disclosures in WO9321932, EP1992345, EP0664701, WO9602262, WO9204893 and WO2016196205.

SUMMARY OF THE INVENTION

The invention relates to a liquid oral pharmaceutical dosage form, comprising two liquids with different active pharmaceutical ingredients (APIs), being physically separated from each other, wherein one of the liquids is an aqueous liquid and the other a hydrophobic/lipophilic liquid, i.e., a two-compartments dosage form. However, one problem with such a dosage form is stability of the liquids, both chemical as well as physical stability. The ingredients need to be chemically compatible with each other as well as chemically stable. The suspensions should have physical stability to reduce sedimentation during shelf life or easily allow for redispersion when simply mixed/shaken before administration.

In addition, the two liquids need to have matched rheological profiles with respect to each other, to be able to fill the package in a production plant and allow for a simple and equivalent emptying and dose uniformity upon use.

The excipients have been chosen to not have an off-note taste by themselves and they may further contribute to taste masking of the active pharmaceutical ingredients (API) or at least do not increase negative perception of the API's off note taste.

The excipients must be acceptable for pharmaceutical oral administration, i.e., nontoxic, nonirritant etc. and being administrated within acceptable daily intake amounts.

In a first aspect the invention relates to a liquid oral pharmaceutical dosage form, comprising a) pharmacologically effective amounts of at least one histamine H2 receptor antagonist in a hydrophobic/lipophilic liquid substantially free from water and comprising at least one viscosity enhancing agent and b) pharmacologically effective amounts of one or more antacid(s) in a liquid comprising at least one viscosity enhancing agent, wherein a) and b) are physically separated.

A ready to use dosage form, consumer friendly, no need to be stored in a refrigerator as well as suitable for people on the go. A small discrete dosage form easy to ingest and which protect the histamine H2 receptor antagonist, such as famotidine from being degraded. The rheological qualities of the liquids in a) and b) should be the same to secure that the histamine H2 receptor antagonist and the antacid(s) having the same behavior and provide the same experience to the consumer upon use.

In a second aspect the invention relates to a two compartments stick pack och a two-compartments sachet comprising the liquid oral pharmaceutical dosage forms.

In a final aspect the invention relates to a method of treating a gastric disease or disorder by use of the liquid oral pharmaceutical dosage form comprising pharmacologically effective amounts of at least one histamine H2 receptor antagonist and pharmacologically effective amounts of one or more antacids as disclosed in the application.

BRIEF DESCRIPTION OF THE DRAWING

FIG. 1 illustrates the behavior results of different mixtures of excipients from Example 4.

DETAILED DESCRIPTION OF EMBODIMENTS OF THE INVENTION

Definitions

In the context of the present application and invention the following definitions apply:

The terms "physical barrier", "physically separated" are intended to mean that the histamine H2-receptor antagonist is separated from the antacid so that they have no contact at all during shelf life. The physical barrier prevents that the histamine H2-receptor antagonist gets in contact with any component that could change and or degrade the histamine H2-receptor antagonist during the shelf life.

The term "substantially free from water or free from water" is intended to mean that the content of water present in the composition is less than about 2 w % based on the total wt. % of the composition, such as less than 1.5, 1, 0.5, 0.4, 0.3, 0.2 or less than 0.1 or totally free from water, i.e., 0 wt % based on the total wt. % of the composition.

The term "% w/w" is intended to mean the percentage of an ingredient(s)/the total percentage by weight of the composition (100%).

The term "histamine H2-receptor antagonist" is intended to mean an agent that inhibit histamine action and therefore reduce gastric secretion of the amount of acid produced and which is pharmacologically accepted.

The term "antacids" is intended to mean agents that function by neutralizing gastric acid and which is pharmacologically accepted.

The term "viscosity enhancing agent" is intended to include viscosity modifier.

The term "matching rheological profiles" is intended to mean that the two liquids have matched rheological profiles to allow for effective filling process during manufacturing of the product and comfortable simultaneous administration of the two liquids when opening the two compartments as well as the compartments should be sufficiently emptied to allow administration of the correct dose.

The term "Medium Chain Triglyceride(s) (MCTs)" is/are intended to mean triglycerides whose fatty acids have an aliphatic tail of 6-12 carbon atoms. The fatty acids found in MCTs are called medium-chain fatty acids (MCFAs). Like all triglycerides, MCTs are composed of a glycerol backbone and three fatty acids. In the case of MCTs, 2 or 3 of the fatty acid chains attached to glycerol are medium-chain in length. Examples includes, hexanoic acid (C6:0, common name caproic acid), octanoic acid (C8:0, common name caprylic acid), and decanoic acid (C10:0, common name capric acid) as well as dodecanoic acid (C12:0, common name lauric acid).

The term "pharmaceutically effective amount" includes an amount effective, at dosage and for periods of time necessary, to achieve the desired results. An effective amount of a compound may vary according to factors, such as intended posology, the disorder or disease state, age and weight of the subject.

The term "gastric disease or disorder" is primarily intended to mean an increased production of the acid secretion which leads to heartburn and bothersome gas symptoms in a subject also named indigestion. Indigestion, also known as dyspepsia, is a condition of impaired digestion. Symptoms may include upper abdominal fullness, heartburn, nausea, belching, or upper abdominal pain. People may also experience feeling full earlier than expected when eating. Dyspepsia is a common problem and is frequently caused by gastroesophageal reflux disease (GERD) or gastritis.

Liquid Oral Pharmaceutical Dosage Form

The invention relates to a liquid oral pharmaceutical dosage form, comprising pharmacologically effective amounts of at least one histamine H2-receptor antagonist and pharmacologically effective amounts of one or more antacid, wherein there is a physical barrier in between the histamine H2-receptor antagonist and the antacid(s). The liquid dosage form is the first liquid dosage form in which a histamine H2-receptor antagonist is stable over time.

The at least one histamine H2-receptor antagonist and the one or more antacid are physically separated from each other, i.e., not get in contact prior to that the subject consumes the liquid oral pharmaceutical dosage form to protect the histamine H2-receptor antagonist from degradation.

The histamine H2-receptor antagonist is in a hydrophobic/lipophilic liquid being substantially free from water and at least one viscosity enhancing agent. The hydrophobic/lipophilic liquid may be an oil or a mixture thereof. Examples include medium chain triglycerides, olive oil, coconut oil, flaxseed oil, palm oil, palm kernel oil, ethyl oleate or a synthetic oil. The oil may also be a super refined oil such as castor oil, corn oil, cottonseed coil, peanut oil, safflower oil, sesame oil, medium chain triglycerides or soybean oil. By super refined oil is for example meant that the polar impurities present in triglycerides are usually comprised of monoglycerides, diglycerides, free fatty acids, plant sterols, coloring matter (chlorophyll, carotene) and oxidation products as well as other polar substances such as environmental chemicals are removed from the oil, which gives some new characteristics to the oil. Super refined oils may be obtained from Croda International Inc. (crodahealthcare.com).

The viscosity enhancing agent suitable to be used in the hydrophobic/lipophilic liquid is selected from the group consisting of ethyl cellulose, Lauroyl polyoxyl glycerides, such as Lauroyl polyoxyl-32-glycerides glycerol dibehenate, glyceryl distearate, cellulose ethyl ether, fumed silica, e and soybean oil, polyglyceryl-3-dioleate or mixtures thereof. Preferably glycerol dibehenate or cellulose ethyl ether or a mixture thereof. glycerol dibehenate may be present in an amount from about 1 to about 10% w/w, such as from about 2 to about 6% w/w, such as 2.5, 3.0, 3.5, 4.0, 4.5, 5.0, 5.5% w/w and cellulose ethyl ether in an amount of from about 0.5 to about 6% w/w, such as from about 0.8 to about 2.5% w/w, such as 1.0, 1.2, 1.4, 1.6, 1.8, 2.0, 2.2, 2.4% w/w.

Simethicon or dimethicone or mixtures thereof may also be used either to replace or together with the hydrophobic/lipophilic liquid, as well as acting as an antifoaming agent to reduce bloating, discomfort and pain.

The hydrophobic/lipophilic liquid may further contain one or more excipients or pH regulating agents, such as sweeteners, flavors, cooling agents, preservatives or colorants. Examples of excipients that are useful are mentioned below. One of the purposes is to provide a dosage form which gives a smooth coating of the throat.

The H2 receptor antagonist is selected from the group consisting of cimetidine, ranitidine, nizatidine, roxatidine and famotidine, their pharmaceutically acceptable salts, isomers and salts of isomers. One example is famotidine (see the examples below).

The one or more antacid may be selected from the group consisting of calcium carbonate, sodium bicarbonate, magnesium hydroxide, aluminum hydroxide, magnesium oxide, magnesium carbonate, aluminum phosphate, magaldrate, magnesium trisilicate, such as selected from the group consisting of calcium carbonate, sodium bicarbonate, magnesium hydroxide and aluminum hydroxide. One example is the combination of calcium carbonate and magnesium hydroxide or aluminum hydroxide and magnesium hydroxide.

The antacids may be in an aqueous-based liquid comprises one or more excipients and/or a pH adjusting agent.

To achieve matching rheological profiles of the two liquids it is suitable in the aqueous based liquid to use one or more viscosity enhancing agents such as polysaccharides, cellulose, carboxy methyl cellulose sodium and microcrystalline cellulose or mixtures thereof. Other examples of agents are vegetable gum such as xanthan gum, alginate, guar gum, carrageenan, gellan, gum, locust bean gum, poly vinyl pyrrolidone, hydroxy ethyl cellulose, hydroxy propyl cellulose, microcrystalline cellulose and cellulose powders or mixtures thereof or synthetic versions thereof.

The amount of xanthan gum is from about 0.05 to about 0.5% w/w such as 0.1, 0.12, 0.2, 0.25, 0.3, 0.38, 0.4% w/w and the amount of carboxy methyl cellulose sodium and microcrystalline cellulose (Avicel CL 611®) is from about 0.4 to about 2% w/w, such as 0.5, 0.6, 0.62, 0.63, 0.7, 0.0.71, 0.8, 0.85, 0.9, 1.0, 1.1, 1.2, 1.25, 1.5, 1.6, 1.7, 1.8, 1.9% w/w.

Alternatively the antacids may be in a hydrophobic/lipophilic liquid being substantially free from water. The hydrophobic/lipophilic liquid may be an oil or a mixture thereof. Examples include medium chain triglycerides, olive oil, coconut oil, flaxseed oil, palm oil, palm kernel oil, ethyl oleate or a synthetic oil. The oil may also be a super refined oil such as castor oil, corn oil, cottonseed coil, peanut oil, safflower oil, sesame oil, medium chain triglycerides or soybean oil. By super refined oil is for example meant that the polar impurities present in triglycerides are usually comprised of monoglycerides, diglycerides, free fatty acids, plant sterols, coloring matter (chlorophyll, carotene) and oxidation products as well as other polar substances such as environmental chemicals are removed from the oil, which gives some new characteristics to the oil. Super refined oils may be obtained from Croda International Inc. (http://www.crodahealthcare.com). Famotidine may be formulated with other active ingredients like simethicone to control gas or alginic acid or salts thereof to act as a physical barrier.

Simethicon it dimethicone or mixtures thereof and other solvents/excipients may also be used to replace or together with the hydrophobic/lipophilic liquid as well as acting as an antifoaming agents to reduce bloating, discomfort and pain.be in a hydrophobic/lipophilic liquid, such as those mentioned above related to the H2 receptor antagonist.

Example of flavors suitable for the histamine H2 receptor antagonist liquid and/or the antacid(s) liquid includes peppermint, licorice, herbs, bubble gum, vanilla, caramel, red berries, such as strawberry, black current, blue berry and cherry, mint and lemon.

The liquid compositions of the invention are suspensions containing the active ingredients in admixture with pharmaceutically acceptable excipients typically found in suspensions for oral administration. Such excipients may be suitable suspending agents, for example, sodium alginate, polyvinylpyrrolidone, gum tragacanth, gum acacia, xanthan gum, locust bean gum and cellulose derivatives such as sodium carboxymethylcellulose, microcrystalline cellulose, hydroxy ethylcellulose, methyl cellulose or hydroxypropyl methylcellulose or mixtures thereof. Also included may be dispersing or wetting agents such as sorbitan esters or lecithin, antigelling additives, surface modifiers, aqueous or non-aqueous vehicles such as sorbitol solution, ethyl alcohol or fractionated vegetable oils, or diluents.

Sometimes if necessary a preservative component may be used. Such a preservative component may be selected from any pharmaceutically acceptable preservative. The alkyl esters of para-hydroxybenzoic acid (the parabens, e.g. butylparaben, methylparaben and propylparaben) are examples and may be used alone or in combination. Generally, the parabens are used in a concentration of about 0.02% w/w. Other preservatives include ethylenediamine tetra-acetic acid, propyl-p-hydroxybenzoates, antioxidants or sorbic acid.

The compositions may also contain colorants and/or sweeteners as appropriate. The sweetening agents may be for example bulk sweeteners such as sugars (e.g. sucrose or fructose) or polyols (e.g. maltitol, xylitol, sorbitol, sucralose) and/or intense sweeteners such as saccharin, aspartame or acesulfame K.

Other active agents may be added to the preparation. For instance, alginate, antiflatulents, analgesics, antidiarrhea, antispasmodic agents or anti-foaming agents like simethicone may be added as well as other gastrointestinal agents in dosage amounts conventionally used in the treatment of gastrointestinal dysfunction, including indigestion.

Examples of liquid oral pharmaceutical dosage form include two-compartment sachets or stick-packs, wherein one of the compartments comprises H2 receptor antagonist, such as famotidine and the other compartment comprises one or more antacids. The compartments can be separated from each other by means of a perforation line, and be provided with an easy opening on one side.

In one embodiment the liquid oral pharmaceutical dosage form, comprising
 a) pharmacologically effective amounts of famotidine in MCT substantially free from water and further comprising viscosity enhancing agents being a mixture of glycerol dibehenate and cellulose ethyl ether.
 b) pharmacologically effective amounts of calcium carbonate and magnesium hydroxide in a liquid, at least one viscosity enhancing agent and at least one flavor, wherein a) and b) are physically separated from each other and wherein a) and b) have matching rheological profiles.

Dosage of the Liquid Oral Pharmaceutical Dosage Form

The histamine H2-receptor antagonist such as famotidine may be present in an amount of from about 2 mg to about 30 mg, such as 4 mg to 20 mg or 8 mg to 12 mg or 2, 3, 4, 5, 6, 7, 8, 9, 10, 11, 12, 13, 14, 15, 16, 17, 18, 19, 20, 21, 22, 23, 24, 25, 226, 27, 18, 19 or 30 mg.

The antacid may be present in an amount of from about 200 to about 3 000 mg. If two different antacids are utilized they may be in the same amount or different amounts depending on the specific combinations. Examples are a liquid oral pharmaceutical dosage form having calcium carbonate in an amount from about 400 to about 1000 mg, such as 600, 700, 800, 900 or 1000 mg and magnesium hydroxide may be present in an amount from about 50 to about 300 mg, such as about 100-about 200 mg, such as 100, 110, 120, 130, 140, 150, 160, 165, 170, 180 190 or 200 mg. If aluminum oxide is used it will be used in an amount from about 200 to about 600 mg, such as 300, 400, 416, 500 or 600 mg.

The liquid in respectively a) or b) may be in an amount of from about 2 to about 20 ml, such as about 2 to about 10 ml, such as 2, 3, 4, 5, 6, 7, 8, 9 or 10 ml. The amount in a) and b) may be the same or different depending on how a) and b) are formulated as well as depending on the form of the dosage form.

The invention also relates to a package comprising multiple liquid oral pharmaceutical dosage forms as defined above.

Finally the invention relates to a method of treating a gastric disease or disorder by use of the liquid oral pharmaceutical dosage form as disclosed above.

In order to further illustrate the present invention and the advantages thereof, the following specific examples are given, it being understood that these examples are intended only to be illustrations without serving as a limitation on the scope of the present invention.

EXAMPLES

Example 1

Materials

All oils were obtained from Croda International.

Magnesium hydroxide and Calcium carbonate were obtained from Magnesia Gmbh.

Famotidine was obtained from Gedeon Richter in Hungary and film coated in-house using conventional coating technology, well known for a person skilled in the art.

|  | Ethocel Standard 45 Premium | Compritol 888 Pellets | CRODAMOL ™ GTCC |
|---|---|---|---|
| Supplier Chemical names | Dow Cellulose, ethyl ether | Gattefossé Glycerol dibehenate EP/Glyceryl dibehenate NF/Ch. P. | Croda Triglycerides, Medium-Chain: mixed ester consisting primarily of caprylic (C8) and capric (C10) acids derived from either coconut or palm oi |
| INCI | ethylcellulose | GLYCERYL BEHENATE GLYCERYL DIBEHENATE TRIBEHENIN | Caprylic/Capric Triglyceride |
| CAS # | 9004-57-3 | 30233-64-8, 91052-55-0, 6916-74-1, 94201-62-4, 18641-57-1 | 73398-61-5, 65381-09-1 |

Formulations

Different kinds of formulations were produced and shown in Table 1.

Famotidine was mixed in different kinds of solvents including different oils to investigate which oils being suitable to be used together with famotidine (Sample 1-11 and 22-25 in Table 1). The results indicated that famotidine is stable in all oils but were most stable in the presence of Medium Chain Triglycerides (Sample 8F1/F2, 22C, 23A/B, 24 A and 25B7).

Different kinds of antacid mixtures where investigated to identify which could be suitable (Sample 12-21 in Table 1).

Two Compartment Package

A two compartment package, where produced being a double compartment sachet made from laminated aluminum foil. Three layers of aluminum foil were sealed to each other to create the two compartment package to be filled with the different formulations. The sachet was produced to allow opening of both compartments simultaneously. 5 ml of Sample 8 (uncoated famotidine) were introduced in one of the compartments and 5 ml of sample 12 were introduced into the other compartment. The two compartment package was sealed.

TABLE 1

| Sample | Sample composition | Amount |
|---|---|---|
| 1 A/B | FMT uncoated + Glycerol | 250 mg + 50 ml/500 mg + 50 ml |
| 2 A/B | FMT uncoated + Glycerol | 125 mg + 25 ml/250 mg + 25 ml |
| 3 A1/A2 | FMT uncoated/coated + Super refined Safflower oil | 25 mg + 5 ml/290 mg + 5 ml |
| 4 B1/B2 | FMT uncoated/coated + Super refined Cottonseed oil | 25 mg + 5 ml/290 mg + 5 ml |
| 5 C1/C2 | FMT uncoated/coated + Super refined Soybean oil | 25 mg + 5 ml/290 mg + 5 ml |
| 6 D1/D2 | FMT uncoated/coated + Super refined Corn oil | 25 mg + 5 ml/290 mg + 5 ml |
| 7 E1/E2 | FMT uncoated/coated + Super refined Sesame oil | 25 mg + 5 ml/290 mg + 5 ml |
| 8 F1/F2 | FMT uncoated/coated + Super refined Medium chain triglycerides | 25 mg + 5 ml/290 mg + 5 ml |
| 9 G1/G2 | FMT uncoated/coated + Super refined Ethyl Oleate | 25 mg + 5 ml/290 mg + 5 ml |
| 10 H1/H2 | FMT uncoated/coated + Olive oil | 25 mg + 5 ml/290 mg + 5 ml |
| 11 A | FMT uncoated + PEG + Standard Medium chain triglycerides |  |
| 12 A | Magnesium hydroxide heavy + Calcium carbonate heavy + water | 165 mg + 800 mg + 4035 mg |
| 13 A | Magnesium hydroxide heavy + Calcium carbonate heavy + Methocel HPMC E3 + water | 165 mg + 800 mg + 500 mg + 3535 mg |
| 14 C | Magnesium hydroxide heavy + Calcium carbonate heavy + Methocel HPMC E3 + Sucralose + Acesulfame K + Flavor + Color + water | 165 mg + 800 mg + 500 mg + 30 mg + 15 mg + 50 mg + 5 mg + 3535 mg |
| 15 D | Magnesium hydroxide heavy + Calcium carbonate heavy + Methocel HPMC E3 + water | 165 mg + 800 mg + 1000 mg + 3535 mg |
| 16 A1 | Magnesium hydroxide heavy + Calcium carbonate heavy + Super refined Ethyl Oleate | 165 mg + 800 mg + 5 ml |
| 17 A2 | Magnesium hydroxide heavy + Calcium carbonate heavy + Super refined Medium chain triglycerides | 165 mg + 800 mg + 5 ml |
| 18 B | Magnesium hydroxide heavy + Calcium carbonate heavy + water | 165 mg + 800 mg + 5 ml |
| 19 E/C | FMT uncoated + Simethicone | 10 mg + 2 ml/20 mg + 4 g |
| 20 A | Magnesium hydroxide + Calcium carbonate light + Super refined Medium chain triglycerides | 165 mg + 800 mg + 5 ml |

TABLE 1-continued

| Sample | Sample composition | Amount |
|---|---|---|
| 21 B | Magnesium hydroxide + Calcium carbonate light + Water | 165 mg + 800 mg + 5 ml |
| 22 C | FMT uncoated + Super refined Medium chain triglycerides | 10 mg + 5 ml |
| 23 A/B | FMT uncoated + Super refined Medium chain triglycerides | 5 mg + 20 ml/5 mg + 10 ml |
| 24 A | FMT uncoated + Simethicone + Super refined Medium chain triglycerides | 100 mg + 5000 mg + 24900 mg |
| 25 B7 | FMT uncoated + Standard Medium chain triglycerides | 80 mg + 39 920 mg |

Example 2

Analysis on the stability of famotidine suspended in different oils.

Uncoated famotidine was mixed in one of the following oils Safflower oil (B1), Soybean oil (B2), Sesame oil (B3), Corn oil (B4), Cottonseed oil (B5), Super refined MCT (B6) and standard MCT (B7). 3 samples were prepared for each batch and the samples where incubated at 40/75° C., 50° C. or 60° C. 10 mg famotidine was mixed with 5 g oil. Samples were removed after 14 days, 1 month, 2 month and 3 month and the stability of famotidine evaluated.

For the stability analysis the samples were prepared and analyzed using the method below Solutions

| Buffer (50 mM Sodium/Potassium Phospate, pH 6.2) | |
|---|---|
| di-Sodiumhydrogen phosphate ($Na_2HPO_4$) dehydrate (g) | 1.64 |
| Potassium phosphate monobasic ($K_3PO_4$) (g) | 5.55 |
| Milli-Q up to (ml) | 1000 |

| Diluent | |
|---|---|
| Methanol (ml) | 200 |
| Buffer up to (ml) | 1000 |

Mobile Phases

| Mobile Phase A | |
|---|---|
| Buffer (ml) | 200 |
| Milli-Q (ml) | 780 |
| Acetonitrile (ml) | 20 |
| Potassium hexafluorophospate ($KPF_6$) (g) | 7.36 |
| Mix and filtrate (nylon 0.45 μm filter) | |

| Mobile phase B | |
|---|---|
| Buffer (ml) | 200 |
| Milli-Q (ml) | 100 |
| Acetonitrile (ml) | 700 |
| Potassium hexafluorophospate ($KPF_6$) (g) | 7.36 |
| Mix and filtrate (nylon 0.45 μm filter) | |

Famotidine Standards

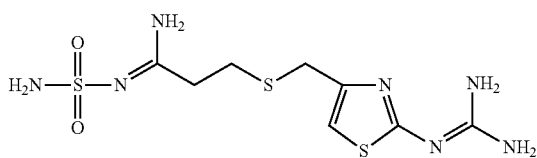 [SMILES: NC(N)=Nc1nc(CSCC/C(N)=N/S(N)(=O)=O)cs1]

Famotidine: CAS nr: 76824-35-6, $C_8H_{15}N_7O_2S_3$, MW: 337.45

| Fam Stock (400 μg FAM/ml) | |
|---|---|
| Famotidine (mg) in 200 ml volumetric flask | 80 |
| Metanol (ml) | Ca 125 |
| Dissolve with ultrasound bath | |
| Methanol upp till (ml) | 200 |

| Fam Std (80 μg/ml) | |
|---|---|
| Fam Stock (ml) | 20 |
| Buffert up to (ml) | 100 |

| Fam Std (40 μg/ml) | |
|---|---|
| Fam std (80 μg/ml) | 10 |
| Diluent up to (ml) | 20 |

| Fam Std (8 μg/ml) | |
|---|---|
| Fam std (80 μg/ml) (ml) | 1 |
| Diluent up to (ml) | 10 |

| SST | |
|---|---|
| SST (Ph.Eur Fam SST) | 1 speck |
| Diluent up to (ml) | 1 |

Sample Preparation
  Pour sample of sample bottle into a 100 ml volumetric flask.
  Rinse the vial at least 3 times with diluent to the volumetric flask.
  Fill the volumetric flask to about 70 ml with diluent.
  Shake the sample for 45 minutes.
  Fill the volumetric flask up to 100 ml with diluent.
  Mix the sample.
  Filter the sample and transfer to LC-vial for LC-UV analysis. (MilleX HV Hydrophilic PVDF 0.45 μm)

Instrument Parameters

| Column: | ACE, C8, 3 μm, 150 mm × 4.6 mm | | |
|---|---|---|---|
| Flow: | 1.0 ml/min | | |
| Gradient: | Time(min) | % MobfasA | % MobfasB |
| | 0.0 | 100 | 0 |
| | 1.0 | 100 | 0 |
| | 16.0 | 35 | 65 |
| | 16.1 | 100 | 0 |
| | 18.0 | 100 | 0 |
| Injection volume: | 10 μl | | |
| Column temp: | 35° C. | | |
| Detection: | UV, 278 nm | | |

| | | Assay | | | | |
|---|---|---|---|---|---|---|
| Sample No | Storage Cond | 0 | 14 days | 1 month | 2 months | 3 months |
| B1 | 40/75 | 93% | 98% | 95% | 84% | 90% |
| B1 | 50° C. | 93% | 99% | 91% | 88% | Na |
| B1 | 60° C. | 93% | 96% | 94% | 82% | Na |
| B2 | 40/75 | 98% | 88% | 81% | 81% | 85% |
| B2 | 50° C. | 98% | 102% | 92% | 81% | Na |
| B2 | 60° C. | 98% | 93% | 93% | 72% | Na |
| B3 | 40/75 | 96% | 84% | 97% | 88% | 87% |
| B3 | 50° C. | 96% | 101% | 95% | 84% | Na |
| B3 | 60° C. | 96% | 98% | 88% | 68% | Na |
| B4 | 40/75 | 91% | 88% | 90% | 77% | 84% |
| B4 | 50° C. | 91% | 90% | 84% | 80% | Na |
| B4 | 60° C. | 91% | 78% | 87% | 74% | Na |
| B5 | 40/75 | 101% | 96% | 93% | 84% | 80% |
| B5 | 50° C. | 101% | 100% | 91% | 73% | Na |
| B5 | 60° C. | 101% | 99% | 93% | 81% | Na |
| B6 | 40/75 | 103% | 104% | 98% | 93% | 99% |
| B6 | 50° C. | 103% | 99% | 97% | 88% | Na |
| B6 | 60° C. | 103% | 98% | 95% | 85% | Na |
| B7 | 40/75 | 103% | 104% | 101% | 100% | 103% |
| B7 | 50° C. | 103% | 103% | 101% | 96% | Na |
| B7 | 60° C. | 103% | 101% | 99% | 92% | Na | na means not analysed

The results from the stability test showed that famotidine in stable in all oils but most stable when mixed with a MCT oil either standard purity or refined MCT (sample B6 and B7).

Example 3

Evaluation of different antacid formulation for their viscosity and consistency.

Different amounts of Xanthan Gum 180 and Avicel CL 611 NF were used.

TABLE 2

| | | Sample | | | | | | | | | |
|---|---|---|---|---|---|---|---|---|---|---|---|
| Ingredients | Purpose | TE007 % ww | TF0035 % ww | TF0036 % ww | TF0042 % ww | TF0043 % ww | TF0053 % ww | TF0054 % ww | TF0055 % ww | TF0056 % ww | TF0057 % ww |
| Calcium carbonate, CalEssence 70, | Active | 10.67 | 14.34 | 25.72 | 14.18 | 14.29 | 14.29 | 14.25 | 14.27 | 14.33 | 14.36 |
| Magnesium hydroxide, Magnesia 725 | Active | 2.21 | 2.96 | 5.31 | 2.93 | 2.95 | 2.95 | 2.94 | 2.94 | 2.96 | 2.96 |
| Sorbitol | Sweetener | 10.17 | 9.12 | 8.18 | 9.01 | 9.08 | 9.08 | 9.06 | 9.07 | 9.11 | 9.13 |
| Xylitol crystalline | Sweetener | 0.55 | 0.49 | 0.44 | 0.49 | 0.49 | 0.49 | 0.49 | 0.49 | 0.49 | 0.49 |
| Xanthan Gum 180 | Viscosity enhancing agent | 0.14 | 0.13 | 0.11 | 0.12 | 0.13 | 0.13 | 0.12 | 0.13 | 0.25 | 0.38 |

TABLE 2-continued

| Ingredients | Purpose | Sample | | | | | | | | | |
|---|---|---|---|---|---|---|---|---|---|---|---|
| | | TE007 % ww | TF0035 % ww | TF0036 % ww | TF0042 % ww | TF0043 % ww | TF0053 % ww | TF0054 % ww | TF0055 % ww | TF0056 % ww | TF0057 % ww |
| Avicel CL 611 NF | Viscosity enhancing agent | 0.70 | 0.63 | 0.56 | 0.62 | 0.63 | 0.71 | 0.80 | 1.25 | 0.63 | 0.63 |
| Acesulfame K | Sweetener | 0.01 | | | | | | | | | |
| Sucralose | Sweetener | 0.01 | | | | | | | | | |
| Purified water | Solvent | 75.53 | 72.34 | 59.68 | 72.65 | 72.44 | 72.35 | 72.34 | 71.85 | 72.23 | 72.05 |
| Total volume (ml) | | 7500 | 5000 | 2500 | 5000 | 5000 | 5000 | 5000 | 5000 | 5000 | 5000 |

TABLE 3

Formulations with one viscosity modifier

| | | Quantity per unit dose (mg) | | | | Ratio per unit dose (%) | | |
|---|---|---|---|---|---|---|---|---|
| Batch No. | Viscosity enhancing agent | Viscosity modifier mg | Famotidine | oil MCT | Total | Famotidine | Viscosity modifier % | oil MCT |
| TBE0697 | Gelucire 50/13 | 100 | 10 | 2390 | 2500 | 0.4 | 4.0 | 95.6 |
| TDE0722 | | 150 | 10 | 2340 | 2500 | 0.4 | 6.0 | 93.6 |
| SME0669 | | 200 | 10 | 4790 | 5000 | 0.2 | 4.0 | 95.8 |
| TBE0700 | Compritol 888 | 100 | 10 | 2390 | 2500 | 0.4 | 4.0 | 95.6 |
| TDE0721 | ATO | 150 | 10 | 2340 | 2500 | 0.4 | 6.0 | 93.6 |
| TDE0717 | PRECIROL ATO 5 | 35 | 10 | 2455 | 2500 | 0.4 | 1.4 | 98.2 |
| TDE0720 | | 150 | 10 | 2340 | 2500 | 0.4 | 6.0 | 93.6 |
| TDE0718a | GELUCIRE ® | 50 | 10 | 2440 | 2500 | 0.4 | 2.0 | 97.6 |
| TDE0718b | 43/01 (HARD FAT) | 100 | 10 | 2390 | 2500 | 0.4 | 4.0 | 95.6 |
| TDE0719 | Aerosil R972 | 50 | 10 | 2440 | 2500 | 0.4 | 2.0 | 97.6 |
| TDE0723 | Pharma | 150 | 10 | 2340 | 2500 | 0.4 | 6.0 | 93.6 |
| TEE0239 | Ethocel Standard 100 Premium | 150 | 10 | 2340 | 2500 | 0.4 | 6.0 | 93.6 |
| TEE0240 | Ethocel Standard 45 Premium | 150 | 10 | 2340 | 2500 | 0.4 | 6.0 | 93.6 |
| TEE0241 | Geloil SC | 2490 | 10 | 0 | 2500 | 0.4 | 99.6 | 0.0 |

TABLE 4

Formulations with two viscosity modifiers

| | Quantity per unit dose (mg) | | | | | Ratio per unit dose (%) | | |
|---|---|---|---|---|---|---|---|---|
| Batch No. | Compritol 888 ATO | Ethocel Standard 45 Premium | Famotidine | oil MCT | Total | Famotidine | Compritol 888 ATO | Ethocel Standard 45 Premium | oil MCT |
| TL0107 | 150 | 62.5 | 10 | 2277.5 | 2500 | 0.4 | 6.0 | 2.5 | 91.1 |

TABLE 5

Formulations with one viscosity modifier plus Simethicone

| | Quantity per unit dose (mg) | | | | | Ratio per unit dose (%) | | |
|---|---|---|---|---|---|---|---|---|
| Batch No. | Gelucire 50/13 | Simethicone | Famotidine | oil MCT | Total | Famotidine | Gelucire 50/13 | Simethicone | oil MCT |
| TBE0698 | 100 | 125 | 10 | 2265 | 2500 | 0.4 | 4.0 | 5.0 | 90.6 |

Example 4

Rheological analysis of 4 batches of samples to evaluate the behaviors of different mixtures of excipients.

| | Excipients % w/w | | |
|---|---|---|---|
| Batches | Ethocel Standard 45 Premium | Compritol 888 Pellets | MCT Oil Crodamol |
| TL0107 | 2.5 | 6 | 91.5 |
| UD0207 | 0.8 | 2 | 97.2 |
| UD0208 | 2.5 | 2 | 95.5 |
| UD0210 | 0.8 | 6 | 93.2 |

The results are shown in FIG. 1. An increased shear thinning behavior was observed with increasing ratio of Ethocel Standard 45 Premium. The viscosity of Ethocel polymer is known to be stable to high temperatures.

The invention claimed is:

1. A liquid oral pharmaceutical dosage form, comprising
   a) pharmacologically effective amounts of at least one histamine H2-receptor antagonist in a hydrophobic/lipophilic liquid being an oil substantially free from water comprising a first viscosity enhancing agent, wherein the first viscosity enhancing agent is a mixture of glycerol dibehenate and cellulose ethyl ether; and
   b) pharmacologically effective amounts of one or more antacid in a liquid comprising a second viscosity enhancing agent and at least one flavor, wherein the second viscosity enhancing agent is selected from the group consisting of vegetable gum, poly vinyl pyrrolidone, hydroxy ethyl cellulose, hydroxy propyl cellulose, microcrystalline cellulose, cellulose powders and mixtures thereof, wherein both a) and b) are liquid formulations that are physically separated from each other, and wherein a) and b) are adapted for simultaneous administration to a subject in need thereof.

2. The liquid oral pharmaceutical dosage form according to claim 1, wherein the at least one histamine H2 receptor antagonist is selected from the group consisting of cimetidine, ranitidine, nizatidine, roxatidine and famotidine, their pharmaceutically acceptable salts, isomers and salts of the isomers.

3. The liquid oral pharmaceutical dosage form according to claim 2, wherein the at least one histamine H2 receptor antagonist is famotidine.

4. The liquid oral pharmaceutical dosage form according to claim 3, wherein the famotidine is present in an amount of from about 2 to about 30 mg.

5. The liquid oral pharmaceutical dosage form according to claim 1, wherein the glycerol dibehenate is present in an amount of about 1 to about 10% w/w based on the total percentage by weight of the liquid formulation a), and the cellulose ethyl ether is present in an amount of about 0.5 to about 6% w/w based on the total percentage by weight of the liquid formulation a).

6. The liquid oral pharmaceutical dosage form according to claim 1, wherein the oil is selected from the group consisting of medium chain triglycerides, olive oil, coconut oil, flaxseed oil, palm oil, palm kernel oil, ethyl oleate, synthetic oil, castor oil, corn oil, cottonseed coil, peanut oil, safflower oil, sesame oil, and soybean oil.

7. The liquid oral pharmaceutical dosage form according to claim 1, wherein the oil is super refined.

8. The liquid oral pharmaceutical dosage form according to claim 1, wherein the oil is medium chain triglycerides.

9. The liquid oral pharmaceutical dosage form according to claim 1, wherein the one or more antacid is selected from the group consisting of calcium carbonate, sodium bicarbonate, magnesium hydroxide, aluminum hydroxide, magnesium oxide, magnesium carbonate, aluminum phosphate, magaldrate and magnesium trisilicate.

10. The liquid oral pharmaceutical dosage form according to claim 1, wherein the one or more antacid is selected from the group consisting of calcium carbonate, magnesium hydroxide and aluminum hydroxide.

11. The liquid oral pharmaceutical dosage form according to claim 1, wherein the one or more antacid is a combination of calcium carbonate and magnesium hydroxide or a combination of aluminum hydroxide and magnesium hydroxide.

12. The liquid oral pharmaceutical dosage form according to claim 1, wherein the at least one flavor is selected from the group consisting of peppermint, spearmint, eucalyptus, licorice, vanilla, herbs, caramel, berries or mixed berries, mixed fruits, black currant, blue berries, cherry, lemon and mixtures thereof.

13. The liquid oral pharmaceutical dosage form according to claim 1, further comprising simethicone, dimethicone or a mixture thereof or alginate in a) and/or b).

14. The liquid oral pharmaceutical dosage form according to claim 1, wherein the one or more antacid is present in an amount of from about 200 to about 3000 mg.

15. The liquid oral pharmaceutical dosage form according to claim 1, wherein each of the liquid formulations a) and b) is present in an amount of from about 2 to about 20 ml.

16. The liquid oral pharmaceutical dosage form according to claim 1, being in the form of a two-compartment stick pack or two-compartment sachet.

17. A method of treating a gastric disease or disorder comprising orally administering the liquid formulations a) and b) of the liquid oral pharmaceutical dosage form according to claim 1 simultaneously to a subject in need thereof.

18. The liquid oral pharmaceutical dosage form according to claim 1, wherein the vegetable gum is selected from the group consisting of alginate, guar gum, locust bean gum, xanthan gum, carrageenan, gellan gum and mixtures thereof.

* * * * *